United States Patent
Brod

(10) Patent No.: US 10,105,418 B2
(45) Date of Patent: Oct. 23, 2018

(54) ORAL ADMINISTRATION OF TOCILIZUMAB TREATMENT OF AUTOIMMUNE DISEASE

(71) Applicant: Staley A. Brod, Bellaire, TX (US)

(72) Inventor: Staley A. Brod, Bellaire, TX (US)

(\*) Notice: Subject to any disclaimer, the term of this patent is extended or adjusted under 35 U.S.C. 154(b) by 74 days.

(21) Appl. No.: 14/139,122

(22) Filed: Dec. 23, 2013

(65) Prior Publication Data

US 2015/0174063 A1   Jun. 25, 2015

(51) Int. Cl.
| | |
|---|---|
| *A61K 39/395* | (2006.01) |
| *A61K 38/20* | (2006.01) |
| *A61K 38/31* | (2006.01) |
| *A61K 38/34* | (2006.01) |
| *A61K 38/35* | (2006.01) |
| *A61K 38/22* | (2006.01) |
| *C07K 16/28* | (2006.01) |
| *A61K 39/00* | (2006.01) |

(52) U.S. Cl.
CPC .......... *A61K 38/35* (2013.01); *A61K 38/2271* (2013.01); *A61K 38/31* (2013.01); *A61K 38/34* (2013.01); *C07K 16/2866* (2013.01); *A61K 2039/505* (2013.01); *C07K 2317/76* (2013.01)

(58) Field of Classification Search
None
See application file for complete search history.

(56) References Cited

U.S. PATENT DOCUMENTS 8,962,805 B2 * 2/2015 Beirnaert ............... C12N 15/09
                                                          424/130.1
2012/0253016 A1 * 10/2012 Igawa et al. ............... 530/387.1

OTHER PUBLICATIONS

Brod et al. (2008), J.of Neuroimmunology, vol. 193, pp. 106-112.*
Minam et al. (2009), Current Opinion In Rheumatology, vol. 21, pp. 224-230.*
Ochi et al. (2008)., J. Neurol Sci. Vo. 274 (1-2), pp. 1-9.*

* cited by examiner

*Primary Examiner* — Daniel E Kolker
*Assistant Examiner* — Jegatheesan Seharaseyon
(74) *Attorney, Agent, or Firm* — Benjamin Aaron Adler

(57) ABSTRACT

The present invention provides a method for treating or delaying the onset of an autoimmune condition in a human subject comprising orally administering to the subject at an effective dose of tocilizumab.

14 Claims, 7 Drawing Sheets

ORAL ADMINISTRATION OF TOCILIZUMAB TREATMENT OF AUTOIMMUNE DISEASE

BACKGROUND OF THE INVENTION

Field of the Invention

The present invention relates generally to the fields of autoimmune diseases. More specifically, the present invention relates to uses of ingested (orally administered) tocilizumab in the treatment of autoimmune diseases.

Description of the Related Art

The following abbreviations may be used herein. ACTH—Adrenocorticotropin hormone, α-MSH—alpha-melanocyte stimulating hormone; CR-EAE—chronic relapsing experimental autoimmune encephalomyelitis; DTH—delayed type hypersensitivity; DPBS—Dulbecco's phosphate buffered saline, DMARD—disease modifying anti-rheumatic drugs; GALT—gut associated lymphoid tissue; PP—Peyer's Patch; TCZ—tocilizumab; SIRS—soluble immune response suppressor; SPF—specific pathogen free; SST—somatostatin; TCZ—tocilizumab; and $T_{reg}$—T regulatory cell.

EAE is a T cell mediated inflammatory autoimmune process of the CNS that resembles in some aspects the human demyelinating disease multiple sclerosis (MS) (1) and provides a useful animal model for the evaluation of potential therapies for cellular mediated autoimmune diseases (2-4). Ingested proteins such as type I IFN (5), SIRS peptide 1-21 (6), α-MSH (7), ACTH (8) and SST (9) inhibit clinical attacks and inflammation in acute EAE (5, 10).

Overproduction of IL-6 has been implicated in the disease pathology of several inflammatory and autoimmune disorders, including rheumatoid arthritis (RA), Castleman's disease, Crohn's disease and systemic-onset juvenile idiopathic arthritis (11). Tocilizumab is a humanized antihuman IL-6 receptor antibody that recognizes both the membrane-bound and the soluble form IL-6R and specifically blocks IL-6 activity (12).

Phase I and II studies of tocilizumab conducted in children with systemic-onset juvenile idiopathic arthritis revealed that tocilizumab reduced the typical symptoms of inflammation attributable to the continuous elevation of IL-6 and sIL-6R levels in serum (13). In a double-blind, randomised, placebo-controlled, parallel group phase III study, 623 patients with moderate to severe active rheumatoid arthritis had significant improvement after rescue therapy with tocilizumab (14). Tocilizumab monotherapy also provided radiographic benefit in patients with rheumatoid arthritis (15).

In January 2010, tocilizumab (RoActemra®; Chugai/Roche), a first-in-class humanized monoclonal antibody that binds specifically to both sIL-6R and mIL-6R and inhibits IL-6R-mediated signaling was approved for patients with moderate to severe rheumatoid arthritis unresponsive to available DMARDs (11-16).

Parenteral tocilizumab can also be effective in other inflammatory diseases including neuromyelitis optica (NMO) by reducing anti-AQP4 autoantibodies (17). Tocilizumab is currently being explored in a large number of autoimmune conditions (18) and is known to have activity in simian arthritis (19) suggesting cross-reactivity in other mammals.

IL-6 transgenic mice developed severe neurologic disease characterized by tremor, ataxia, and seizure (20). IL-6-deficient mice were completely resistant to MOG EAE (21). IL-6 is elevated in the spinal cord and CSF of mice with active EAE but IL-6 administration was therapeutic (22).

Therefore, the prior art is deficient in the use of oral, ingested tocilizumab in the treatment of autoimmune diseases such as multiple sclerosis. The present invention fulfills this long-standing need and desire in the art.

SUMMARY OF THE INVENTION

The present invention is directed to a method for treating or delaying the onset of an autoimmune condition in a human subject comprising orally administering to the subject an effective dose of tocilizumab.

The present invention is further directed to a method of decreasing innate inflammatory cytokines IL-1β and TNF-α, Th1-like cytokines IL-2 and IFN-γ, IL-17 ($T_{eff}$), IL-12p70 and increasing the Th2-like counter-regulatory cytokine IL-13 in a human subject comprising orally administering to the subject an effective dose of tocilizumab.

BRIEF DESCRIPTION OF DRAWINGS

The following drawings are part of the present specification and are included to further demonstrate certain aspects of the present invention. The invention may be better understood by reference to the drawings in combination with the detailed description of specific embodiments presented herein.

DETAILED DESCRIPTION OF THE INVENTION

Figure 1:
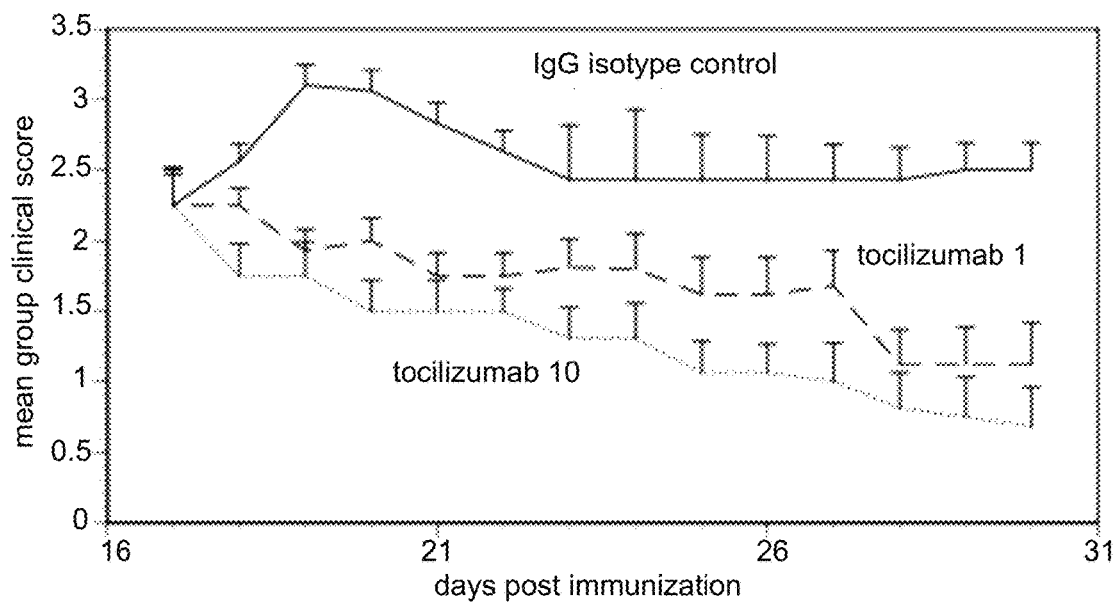
FIG. 1 shows that ingested tocilizumab (TCZ) inhibits clinical EAE attacks. B6 mice (n =8/group) were immunized with MOG peptide 35-55 and were gavaged with 0.1 ml of 1 µg or 10 µg IgG isotype control or 1 mg or 10 mg tocilizumab as described. Both 1 and 10 mg ingested tocilizumab significantly inhibits clinical EAE progression compared to control (p<0.001, ANOVA, day 17-30, group clinical score±SEM). The figure shows combined results from 3 separate experiments (total n=24/group).

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

Treatment of chronic autoimmune disease is challenging even with the advent of new therapeutic techniques. Typical therapies involve the administration of immunosuppressive agents such as steroids. Though steroids are typically not highly effective, they are well tolerated for long term use and many may be administered orally. A non-invasive method for administration, such as oral administration, is highly preferred in cases of chronic diseases such as multiple sclerosis.

The studies described here clearly demonstrate that orally administered and/or ingested tocilizumab can be used as a therapeutic treatment for autoimmune disease. The EAE mouse model is a well established model system for the study of human autoimmune disease, more specifically multiple sclerosis. Studies herein show that tocilizumab may be orally administered to mice over an extended time period with no detectable toxicity. Furthermore, the oral tocilizumab administration significantly reduced clinical symptoms of autoimmune disease as compared to a placebo control in the murine EAE model system. Thus, these studies provide the basis for a new enteral formulations of tocilizumab for the treatment of autoimmune disease.

Clinical severity of disease symptoms (e.g. limb weakness, ataxia, and paraplegia) may be evaluated in various ways. In one embodiment of the invention, clinical severity is graded on a numerical scale corresponding to the number or severity of symptoms observed. In a specific embodiment of the invention, clinical symptoms in a murine model are quantified as follows: 0=no disease; 1=minimal or mild hind limb weakness (associated with limp tail); 2=moderate hind limb weakness or mild ataxia (waddling gait and/or poor righting ability); 3=moderate to severe hind limb weakness; 4=severe hind limb weakness or moderate ataxia; 5=paraplegia with no more than moderate four limb weakness; 6=paraplegia with severe four limb weakness or severe ataxia. In another embodiment of the invention, disease symptoms are evaluated by number of inflammatory foci per CNS segment or area. In a very specific embodiment, these evaluations of inflammatory foci are conducted by direct visual observation of the subject CNS post-mortem.

Mitogen stimulation reflects non-antigen and antigen-specific responses, thus the cytokine profiles of stimulated spleen cells or stimulated CNS lymphocytes may also be used to evaluate disease. Stimulation may be provided by NK (natural killer) and T cell stimulant ConA, or MOG peptide 35-55. Thus, in one embodiment of the invention, disease is evaluated by Th1-like cytokines (e.g. IL-2, IFN-γ, IL12p70, IL-1β, I-TAC, RANTES), Th2-like cytokines (e.g. IL-4, IL-10, IL-13, CD30, SDF-1, TCA-3) and certain specific cytokines referred to as chemokines (e.g. G-CSF, GM-CSF, MIP-1γ, TECK). Cytokines, including chemokines, that may be profiled to evaluate disease include, but are not limited to: BLC, CD30L, eotaxin, eotaxin-2, FAS ligand, fractalkine, G-CSF, GM-CSF, IFN-γ, IL-1α, IL-1β, IL-2, IL-3, IL-4, IL-6, IL-9, IL-10, IL-12p40, IL-12p70, IL-13, IL-17, I-TAC, KC, Leptin, LIX, lymphotactin, MCP-1, M-CSF, MIG, MIP-1-α, MIP-1γ, RANTES, SDF-1, TCA-3, TECK, TIMP-1, TIMP-2, TNF-α, sTNF RI, sTNF RII.

The new methods disclosed herein address one of the greatest obstacles to treating chronic disease such autoimmune disease, that is long term tolerance of the therapeutic regimen. Such tolerance takes into account not only biological tolerance, but also tolerance in patients undergoing therapy. Injectable therapeutics are far from ideal for the treatment of chronic disease. Consent injection can result in lasting damage to the tissues around the injection site and is painful and inconvenient for patients. Additionally, injection of any substance into the body increases the risk for infection by bacteria or viruses that may be present in the therapeutic formulations or on the injection apparatus itself. The instant invention enables methods for oral administration of potent immunomodulatory polypeptides. Surprisingly, these polypeptides remain highly active in an oral formulation and are effective for treating autoimmune disease. These new oral therapeutic polypeptides are particularly well adapted for prolonged administration that is often required for the treatment of chronic disease.

Tocilizumab compositions according to the instant invention may also be used in conjunction with other therapies that are used for the treatment of inflammation and/or autoimmune diseases. Such secondary therapies can include small molecule drugs as well as therapeutic nucleic acids or polypeptides. Anti-inflammatory agents, for example, are agents that decrease signs and symptoms of inflammation. A wide variety of anti-inflammatory agents are known to one of skill in the art. Most commonly used are the nonsteroidal anti-inflammatory agents (NSAIDs) which work by inhibiting the production of prostaglandins. Non-limiting examples include, ibuprofen, ketoprofen, piroxicam, naproxen, naproxen sodium, sulindac, aspirin, choline subsalicylate, diflunisal, oxaprozin, diclofenac sodium delayed release, diclofenac potassium immediate release, etodolac, ketorolac, fenoprofen, flurbiprofen, indomethacin, fenamates, meclofenamate, mefenamic acid, nabumetone, oxicam, piroxicam, salsalate, tolmetin, and magnesium salicylate. Another group of anti-inflammatory agents comprise steroid based potent anti-inflammatory agents, for example, the corticosteroids which are exemplified by dexamethason, hydrocortisone, methylprednisolone, prednisone, and triamcinolone as non-limiting examples. Several of these anti-inflammatory agents are available under well known brand names, for example, the NSAIDs comprising ibuprofen include Advil, Motrin IB, Nuprin; NSAIDs comprising acetaminophens include Tylenol; NSAIDs comprising naproxen include Aleve.

As discussed supra, certain known immunomodulatory polypeptides may also be used in accordance with the invention. Such polypeptides include, but are not limited to, SIRS interferon-α and interferon-τ.

Pharmaceutical compositions of the present invention comprise an effective amount of tocilizumab and optionally at least one additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains an tocilizumab or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, gels (e.g., gelatin), dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

A pharmaceutical composition of the present invention comprising an tocilizumab may also comprise different types of carriers depending on whether it is to be administered in solid, liquid or aerosol form, and whether it need to be sterile. The present invention can be administered intranasally, intravitreally, intravaginally, intrarectally, topically, mucosally, intraocularally, orally, topically, locally, via inhalation (e.g. aerosol inhalation), via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a tocilizumab composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. In the case of proteinacious compositions of the invention, it may also be preferable that the action of proteases be inhibited during storage of such tocilizumab compositions. This can be accomplished by the additional of protease inhibitors and/or the storage of the compositions at low temperature prior to administration.

In embodiments where compositions according to the invention are provided in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof an excipient, such as, for example, dicalcium phosphate, mannitol, lactose, starch, magnesium stearate, sodium saccharine, cellulose, magnesium carbonate or combinations thereof a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Methods of the invention will generally be used in an amount of tocilizumab effective to achieve the intended purpose. For use to treat or prevent a disease condition, tocilizumab, or pharmaceutical compositions thereof, are administered in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein. The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of autoimmune disorders, the drugs that may be used in combination with tocilizumab of the invention include, but are not limited to, steroid and non-steroid anti-inflammatory agents.

Methods for estimating dose conversions between animal models and humans have been developed. In general these algorithms have been used to extrapolate an animal dose to a dose that would be tolerated by a human. For example, method for dose conversions were disclosed by Freireich et al. (1966). The conversion methods taught by Freireich calculate equivalent doses between species using surface area (m.sup.2) rather than mass (kg), a method that correlates much more closely to actual data than body mass conversions. Specifically, Freireich teaches how to use an animal 10% lethal dosage (LD.sub.10) value to estimate the maximum tolerated doses in a human. Freireich also discussed method for converting a dose in mg/kg to a dose in mg/m.sup.2 by using the "km" conversion factor for the given animal. For example, in the case of a laboratory mouse the km is approximately 3.0. Thus, in mice mg/m.sup.2=k.sub.m (3.0 for mice).times.dose in mg/kg.

More recent studies regarding species dose scaling have further elaborated upon the methods of Freireich. These newer studies have reduced error associated with conversion between species to determine human tolerable doses. For example, Watanabe et al. (1992) describes that a conversion of doses between species using body surface area may not be the most accurate method per se for predicting a human equivalent dosage. Nonetheless, the scaling factors set forth by Watanabe yield results that are within the margin of error of the older Freireich conversions. Currently accepted methods for determining a proper starting dose in humans expand upon the methods set forth by Freireich. For example, Mahmood et al. (2003) provides a discussion regarding the choice of a proper starting dose in humans given dose studies in animals.

It is an objective of the present invention to demonstrate that oral tocilizumab has an anti-inflammatory effect in experimental autoimmune encephalomyelitis in vivo by decreasing Th17, Th1-like cytokines, increasing Th2-like cytokines with $T_{reg}$ induction in the CNS target organ in murine experimental autoimmune encephalomyelitis.

As described in detail below, the present invention is directed to a method for treating or delaying the onset of an autoimmune condition in a human subject comprising orally administering to the subject an effective dose of tocilizumab. In one aspect of this method, the tocilizumab is administered in a liquid form. In one aspect of this method, the tocilizumab is administered in a solid form. Representative examples of condition include but are not limited to rheumatoid arthritis, psoriasis, type 1 diabetes, systemic lupus erythematosus, transplant rejection, autoimmune thyroid disease (Hashimoto's disease), sarcoidosis, scleroderma, granulomatous vasculitis, Crohn's disease, ulcerative colitis, Sjogren's disease, ankylosing spondylitis, polymyositis dermatomyositis, polyarteritis nodosa, immunologically mediated blistering skin diseases, Behcet's syndrome, multiple sclerosis, systemic sclerosis, Goodpasture's disease or immune mediated glomerulonephritis. A person having ordinary skill in this are would be able to prepare satisfactory composition of tocilizumab and readily determine appropriate dosages for the condition to be treated. For example, tocilizumab may be administered in a dose from about 1 mg to about 50 mg. In one preferred embodiment, tocilizumab is administered in a dose from about 10 mg. In another preferred embodiment, tocilizumab is administered in a dose from about 10 mcg. Generally, tocilizumab administration decreases levels of IL-1β, IL-2, IL-12p70, IL-13, IL-12, IL-17 ($T_{eff}$), TNF-α and IFN-γ. In a preferred embodiment, tocilizumab may be administered in combination with a drug such as an anti-inflammatory agent, a SIRS peptide, α-MSH, ACTH and SST.

In another embodiment, the present invention also provides a method of decreasing innate inflammatory cytokines IL-1β and TNF-α, Th1-like cytokines IL-2 and IFN-γ, IL-17 ($T_{eff}$), IL-12p70 and increasing the Th2-like counter-regulatory cytokine IL-13 in a human subject comprising orally administering to the subject an effective dose of tocilizumab is administered in a solid form. Representative examples of condition include but are not limited to rheumatoid arthritis, psoriasis, type 1 diabetes, systemic lupus erythematosus, transplant rejection, autoimmune thyroid disease (Hashimoto's disease), sarcoidosis, scleroderma, granulomatous vasculitis, Crohn's disease, ulcerative colitis, Sjogren's disease, ankylosing spondylitis, polymyositis dermatomyositis, polyarteritis nodosa, immunologically mediated blistering skin diseases, Behcet's syndrome, multiple sclerosis, systemic sclerosis, Goodpasture's disease or immune mediated glomerulonephritis. A person having ordinary skill in this are would be able to prepare satisfactory composition of tocilizumab and readily determine appropriate dosages for the condition to be treated. For example, tocilizumab may be administered in a dose from about 1 mg to about 50 mg.

Other objects, features and advantages of the present invention will become apparent from the following. It should be understood, however, that the specific examples, while indicating preferred embodiments of the invention, are given by way of illustration only, since various changes and modifications within the spirit and scope of the invention will become apparent to those skilled in the art from this detailed description.

EXAMPLE 1

Materials and Methods
Induction of Active EAE

C57BL/6 6-8 week old females were actively immunized, maintained, handled and surveiled as outlined (6). Briefly, C57BL/6 6-8 week old females (Jackson Labs, Bar Harbor, Me.) were actively immunized by subcutaneous injection (s.c.) of 0.2 ml inoculum containing 200 mg MOG peptide 35-55 in IFA (DifcoLabs, Detroit, Mich.) with 800 mg *Mycobacterium tuberculosus hominis* H37Ra (MT) on day 0 and 7 following (23), with pertussis toxin (PTx) (List Biologicals) 200 ng i.p. on day 0 and day 2 and followed for evidence of disease. Clinical severity was graded daily as follows by a blinded observer: 0=no disease; 1=minimal or mild hind limb weakness (associated with limp tail); 2=moderate hind limb weakness or mild ataxia (waddling gait and/or poor righting ability); 3=moderate to severe hind limb weakness; 4=severe hind limb weakness or moderate ataxia; 5=paraplegia with no more than moderate four limb weakness; 6=paraplegia with severe four limb weakness or severe ataxia.

Adoptive Transfer

Thirty days after inoculation and after peak score of clinical attack, all spleens from each treatment group were aseptically removed, single cell suspensions prepared, and red cell lysis performed by adding 2-3 ml sterile water to single cells for 5 seconds, and once the solution became transparent, adding AIM-V media to a 50 ml tube. Splenocytes from grouped IgG isotype control fed, 1 μg or 10 μg tocilizumab fed mice were re-stimulated with MOG peptide 35-55 at a final concentration of 10 μg/ml for 48 hours in serum free medium (AIM-V medium, Gibco BRL, Grand Island, N.Y.) with $2\times10^5$ cells/200 ml in triplicate in 96 well U-bottomed plates in a humidified 5% $CO_2$/95% air incubator at 37° C. Splenocytes from control fed mice were also re-stimulated with MOG peptide 35-55 and 50 μg/ml tocilizumab in vitro as described above. $CD4^+$ T cells and monocytes/macrophage were isolated from splenocytes after MOG restimulation above using CD4 (L3T4) MicroBeads, mouse CD11b MicroBeads, human and mouse—monocyte/macrophage lineage (Miltenyi Biotec, Auburn, Calif.). Following incubation, cells were collected, washed twice in PBS, and viability determined by standard Trypan blue exclusion. Viable cells were adjusted to $10^7$ cells/0.5 ml Dulbecco's PBS immediately prior to i.p. injection into active MOG peptide 35-55 immunized recipient mice during ongoing disease (~day 17 post immunization). Following administration of tocilizumab or adoptive transfer, clinical outcome was measured by comparing the difference between group mean active treatment and placebo group scores from day 17-30 post immunization.

Active Protein

Tocilizumab (IgG1) (Actemra®) was purchased from Roche Pharma.

Control Protein

Mouse IgG isotype control antibody (1-10 μg feeding, 50 μg/ml in vitro), was purchased from Southern Biotech, Birmingham, Ala.

Dosing (Feeding) Regimen

Once non-treated inoculated mice attained a clinical score 1.5-2.2, B6 mice were randomized to one of 3 treatment groups, and gavaged (fed) with 0.1 ml of 1 μg or 10 μg mouse IgG isotype control (mock), 1 μg, or 10 μg of tocilizumab using a 2.5 cm syringe fitted with a 22-24 gauge ball point needle (Thomas Scientific, Swedesboro, N.J.) as described (7).

Histology

Following sacrifice, cords were removed and immersion fixed in 10% neutral buffered formalin for a minimum of two weeks. After fixation, cords were sectioned in entirety in the horizontal plane at approximately 3 mm intervals and processed to paraffin. Paraffin blocks were sectioned at 6-8 microns, and step sections were stained with hematoxylin and eosin and examined by light microscopy. Cord sections were evaluated independently for foci of inflammation by an observer (SAB) (blinded) without knowledge of the treatment status of the mice prior to sacrifice. Spinal cord tissue was sampled in an identical fashion for each animal and numbers of inflammatory foci per high-powered field (HPF) (>20 perivascular lymphocytes) in the parenchyma were counted.

Measurement of Cytokine Secretion

Spleens and spinal cords (CNS) from each treatment group were aseptically removed and single cell suspensions prepared. In spinal cords, whole cords were passed through a cell strainer for CNS lymphocytes (B and D, Franklin Lakes, N.J.) and spun at 600 rpm several times to separate lymphocytes from CNS tissue. Spleen leucocytes and cord lymphocytes from grouped IgG isotype control fed or 10 mg tocilizumab fed mice were stimulated with 10 mg MOG peptide 35-55×48 hours as described (6). Murine cytokine responses were examined using a customized RayBio Mouse Cytokine Inflammatory Antibody Array that included innate cytokine IL-6, TNF-α, IL-17 (Teff), Th1-like (IL-2, IFN-γ), Th2-like cytokines (IL-4, IL-10, IL-13) and IL-12p70 using the RayBioantibody array Analysis tool application (RayBiotech, Inc, Norcross, Ga.). Mouse TGF-β was measured using Human/Mouse TGF-β1 ELISA Ready-SET-Go (eBioscience, San Diego, CA). Results were grouped from mice fed IgG isotype control or mice fed with tocilizumab from grouped samples of at least two separate experiments (each sample performed in duplicate) and expressed as pg/ml±SEM (student t-test).

Phenotypic Analysis

CD25 and FoxP3 expression by $CD3^+CD4^+$ lymphocytes was analyzed using the Beckman Coulter 10-Color Gallios Flow Cytometer and mouse regulatory T Cell Staining Kit with PE FoxP3 FJK-16s, FITC CD4, APC CD25 (eBioscience, San Diego, Calif.) following the manufacturer's instructions. Statistical analysis was performed using ANOVA and student t test. (Prism 4.0).

EXAMPLE 2

Results

Oral Tocilizumab Inhibits Active EAE and Donor Cells Transferred from Tocilizumab Fed Mice can Modulate Disease in Actively Immunized Recipients Preliminary experiments determined the immuno-modulatory capability of 1 and 10 mg ingested (orally administered) tocilizumab compared to IgG control in EAE. Mice were immunized and separated into 3 groups once each mouse attained a clinical score ~2.2 (day 17 post immunization) at which time oral dosing was started. The IgG control group increased group clinical score from day 17 and plateaued at clinical score=2.5 after 30 days post immunization and 13 days after the initiation of feeding. Active treatment groups fed with 1 and 10 mg showed significant decreases in group clinical scores after initiation of therapy (day 17) with 10 mg showing the most clinical effect and reduction of disease severity compared to placebo (FIG. 1).

Figure 5A:
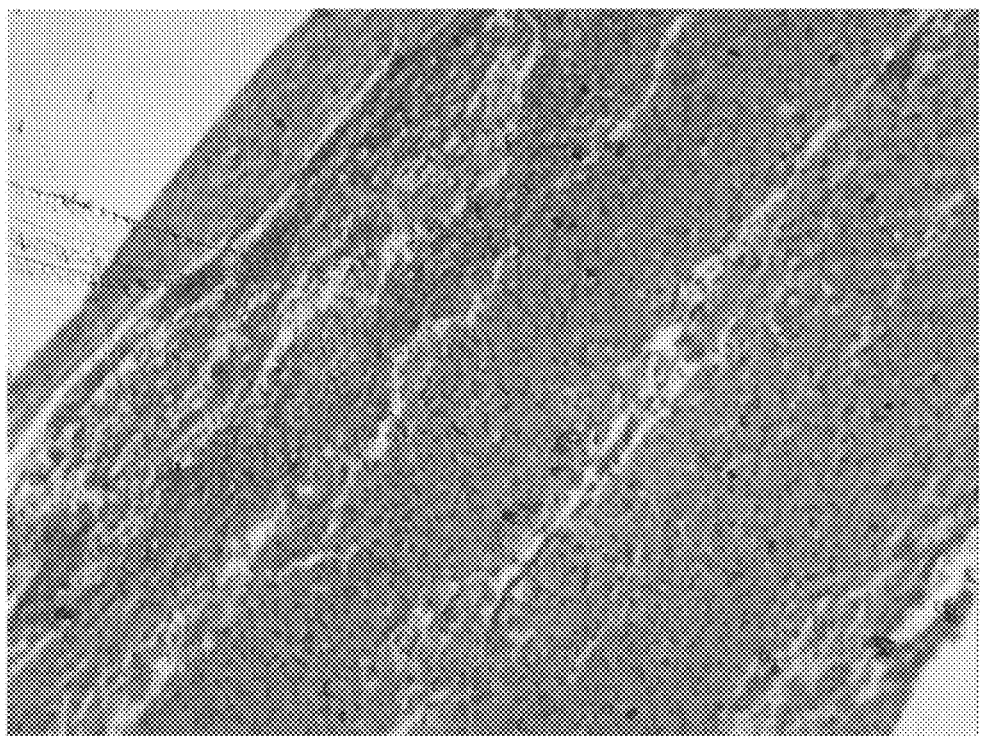
FIGS. 5A-5E shows representative photomicrographs (40×) of MOG peptide 35-55-induced inflammatory lesions in spinal cord of IgG isotype control fed (FIG. 5A), 1 mg tocilizumab fed B6 mice (FIG. 5B), 10 mg tocilizumab fed B6 mice (FIG. 5C), recipients of donor splenic cells from control IgG fed mice (FIG. 5D) and tocilizumab fed mice (FIG. 5E). Cords were prepared. In the active fed group, control (FIG. 5A) shows the most severe inflammation followed by the 10 mg tocilizumab (FIG. 5B) and 1 mg tocilizumab fed group (FIG. 5C). In the adoptive transfer recipients, control (FIG. 5D) shows the most severe inflammation followed by the 10 mg tocilizumab (FIG. 5E). The figures are representative of two separate experiments from FIGS. 1 and 2.
Figure 5B:
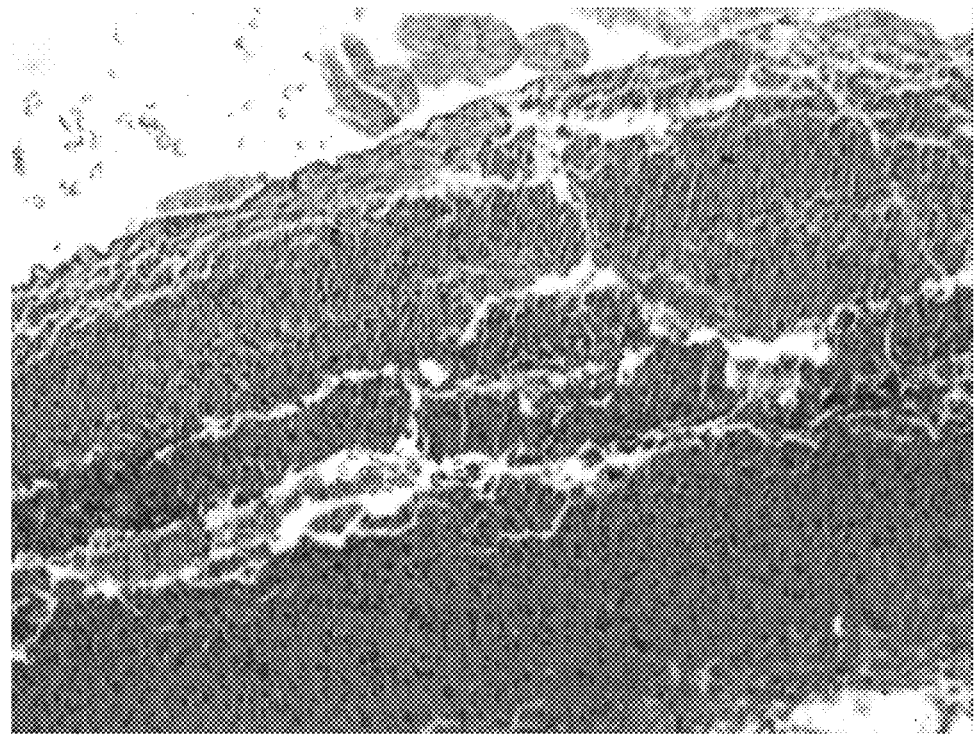
Figure 5C:
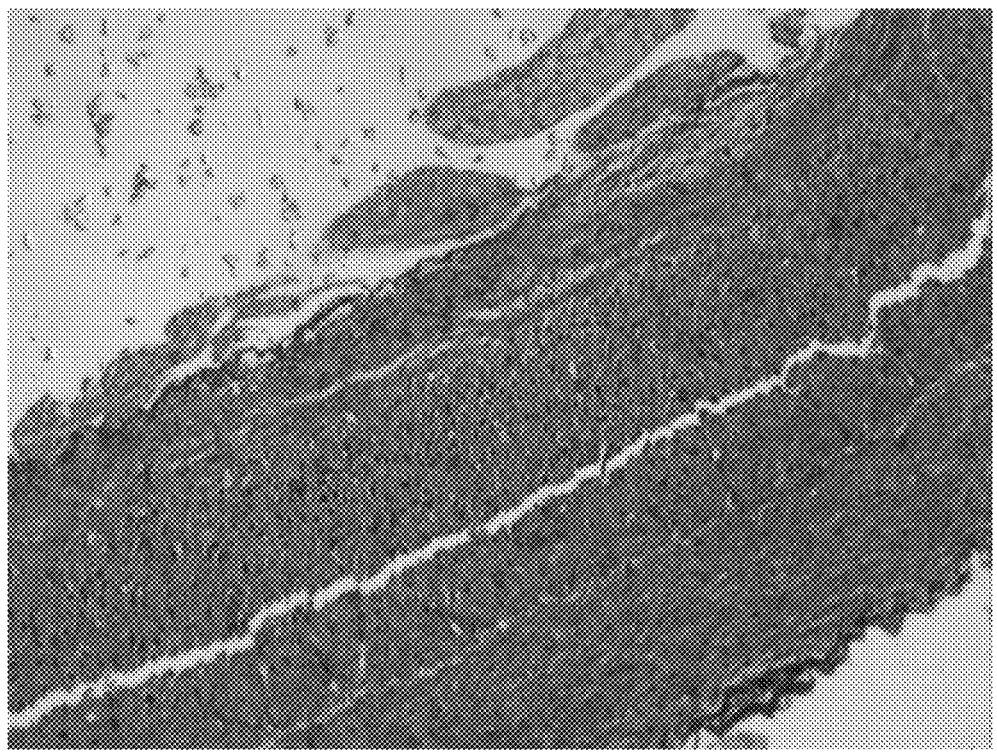

Thirty days following immunization, there were significantly less inflammatory foci in the 1 mg fed group (mean group inflammatory score=3.9±0.16) (FIG. 5B) and in the 10 mg fed group (mean group inflammatory score=3.9±0.28) (FIG. 5C) compared to the IgG control fed group (mean group inflammatory score=6.3±0.5) (FIG. 5A) (p<0.008, ANOVA; n=24/group).

Figure 2:
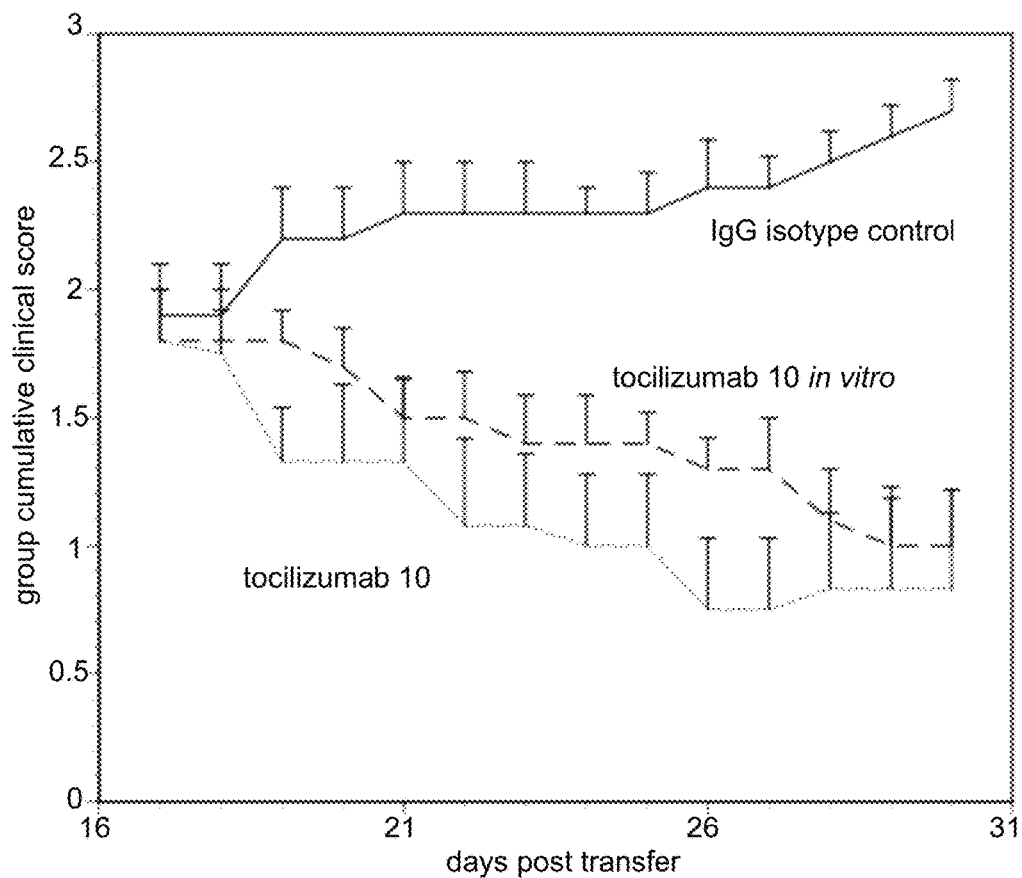
FIG. 2 shows that adoptively transferred donor cells from tocilizumab fed immunized mice protect against active EAE. Thirty days after inoculation and after peak score of clinical attack, spleens from 10 mg IgG control and 10 mg tocilizumab fed mice were isolated and re-stimulated with MOG peptide 35-55 and adoptively transferred. A third group of control spleen cells were re-stimulated with MOG peptide 35-55 and 50 mg/ml tocilizumab in vitro. Recipients of IgG control fed donor cells increased their group clinical disease severity. The in vitro control group 50 mg/ml IgG isotype control is not different from fed IgG control. In contrast, recipients of tocilizumab fed donor cells and donor cells incubated with tocilizumab in vitro decreased their group clinical score significantly compared to recipients of saline control cells (p<0.005, days 17-30, ANOVA, day 17-30, group clinical score±SEM). This experiment shows a combination of 3 separate experiments (total n=24/group).

Whether protection could be passively transferred from tocilizumab fed mice into actively immunized mice was examined. After adoptive transfer of MOG-restimulated splenocytes into actively immunized recipient mice with early clinical disease on day 17 (mean group clinical score ~1.7-1.8), recipients of donor splenocytes from IgG control fed mice increased their group clinical disease severity over 13 days to a maximum of 2.7. In contrast, recipients of donor splenocytes from 10 mg tocilizumab fed mice or from splenocytes incubated with 50 mg/ml tocilizumab in vitro decreased their group clinical score at day 30 to a score=0.83 and 1.0 respectively (FIG. 2). There was a significantly better clinical score with 10 mg tocilizumab fed group vs the 50 mg/ml tocilizumab in vitro group.

Figure 5D:
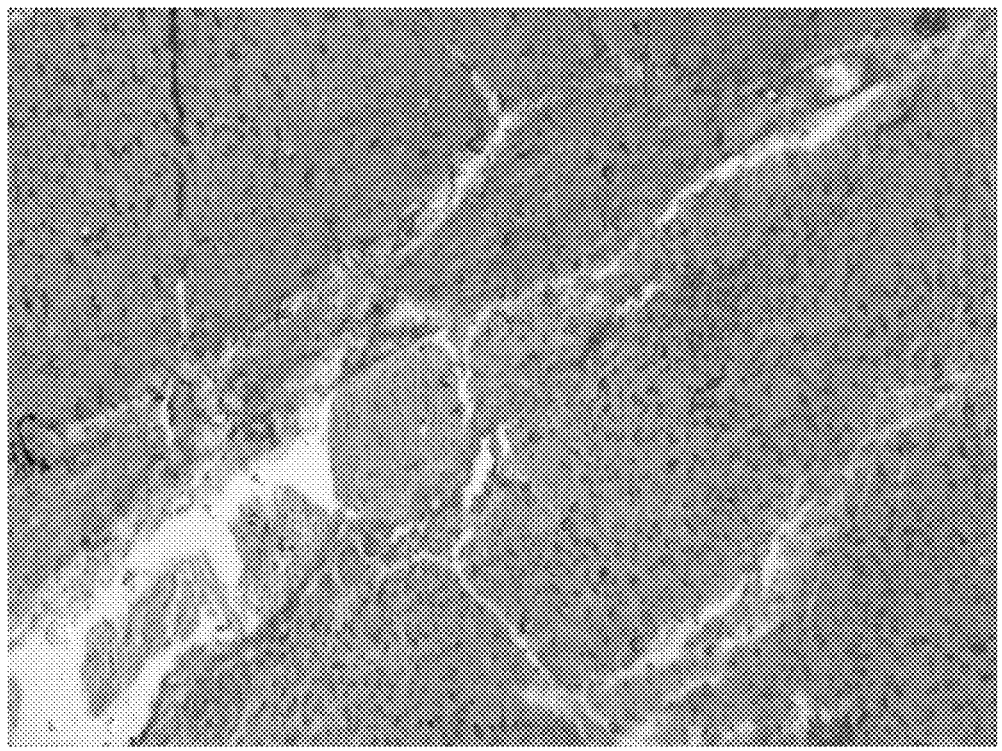
Figure 5E:
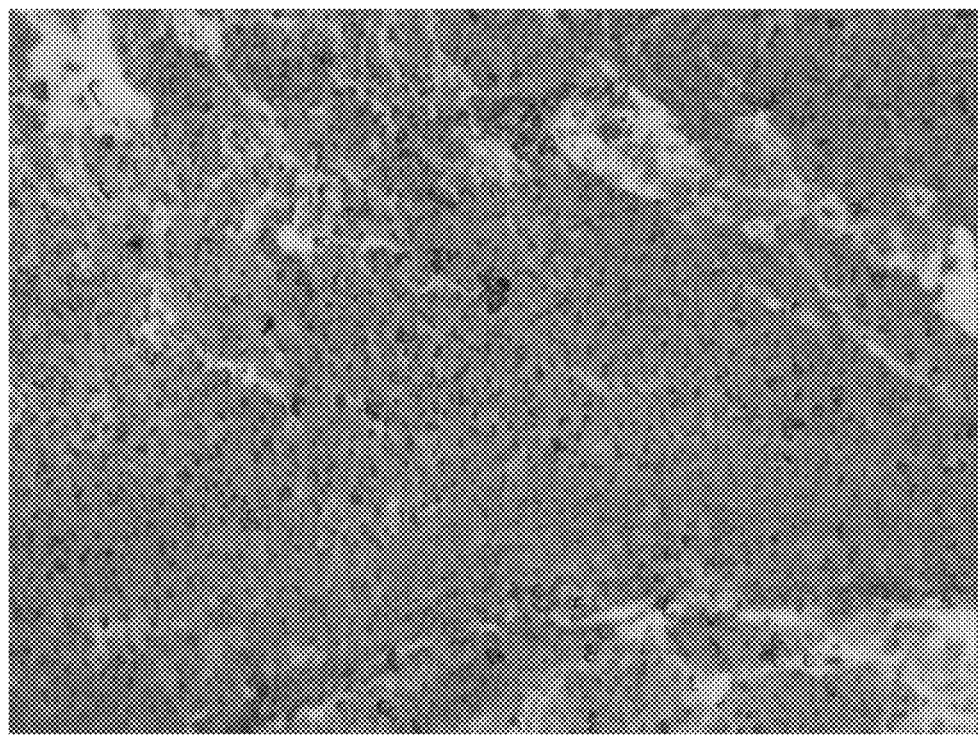

Thirteen days following adoptive transfer, the number of CNS inflammatory foci in the IgG control fed group was significantly higher (mean group inflammatory score=5.5±0.45) (FIG. 5D) compared to either 10 mg tocilizumab fed donors (3.3±0.22) (FIG. 5E) or in vitro tocilizumab treated recipients (3.0±0.32) (p<0.008, ANOVA; n=24/group).

EXAMPLE 3

Figure 3:
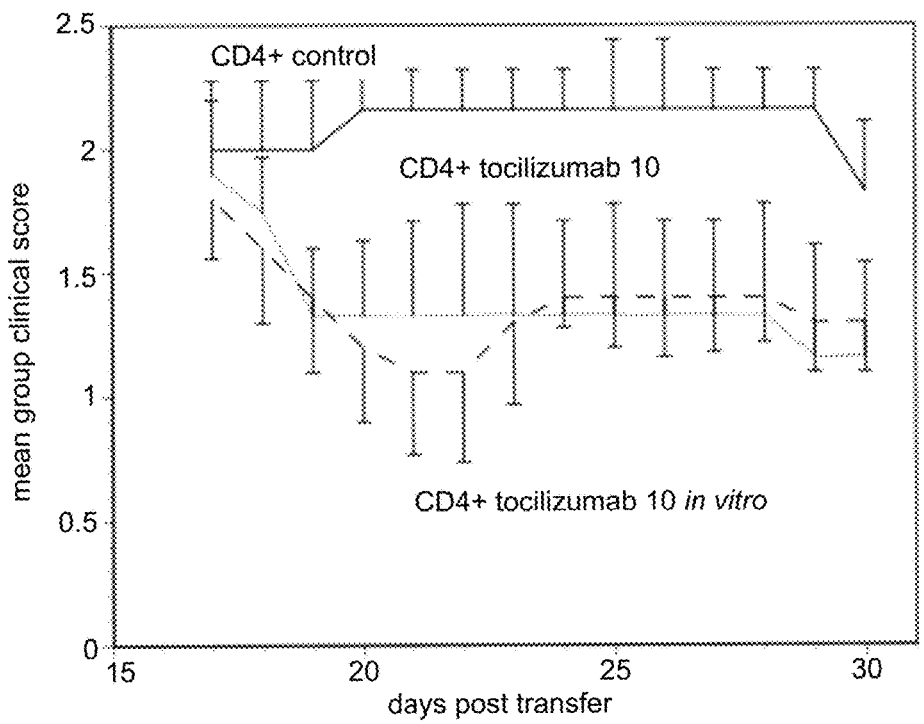
FIG. 3 shows adoptively transferred donor CD4+ T cells from tocilizumab fed immunized mice protect against active EAE. Thirty days after inoculation and after peak score of clinical attack, spleens from IgG control and 10 mg tocilizumab fed mice were isolated and re-stimulated with MOG peptide 35-55, CD4+ T cells isolated and adoptively transferred. A third group of control spleen cells were re-stimulated with MOG peptide 35-55 and 50 mg/ml tocilizumab in vitro and CD4+ T cells isolated before transfer. Recipients of IgG control fed CD4+ T donor cells increased their group clinical disease severity. In contrast, recipients of tocilizumab fed CD4+ T cells donor cells and CD4+ T cells donor cells incubated with tocilizumab in vitro decreased their group clinical score significantly compared to recipients of saline control cells (p<0.005, days 17-30, ANOVA, group clinical score±SEM). The in vitro control group 50 mg/ml IgG isotype control was not different from fed IgG control. This experiment shows a combination of 3 separate experiments (total n=12/group).

Adoptively Transferred $CD4^+$ T and $CD11b^+$ Cells from Tocilizumab Fed Donor Mice can Modulate Disease in Actively Immunized Recipients Whether a T cell subset ($CD4^+$) from a fed donor would show immune-modulatory activity in actively immunized recipients was determined. After adoptive transfer of MOG-restimulated $CD4^+$ T cells isolated from MOG activated splenocytes into actively immunized recipient mice with early clinical disease on day 17 (mean group clinical score ~2.0), recipients of donor $CD4^+$ T cells from IgG control fed mice increased their group clinical disease severity over 13 days to a maximum of 2.2. In contrast, recipients of donor $CD4^+$ T cells from 10 mg tocilizumab fed mice or from donor $CD4^+$ T cells incubated in vitro with 50 mg/ml tocilizumab decreased their group clinical score at day 30 to a score=0.70 and 0.82 respectively (FIG. 3). There was no significant difference between the 10 mg tocilizumab fed group and the 50 mg/ml tocilizumab in vitro group.

Figure 4:
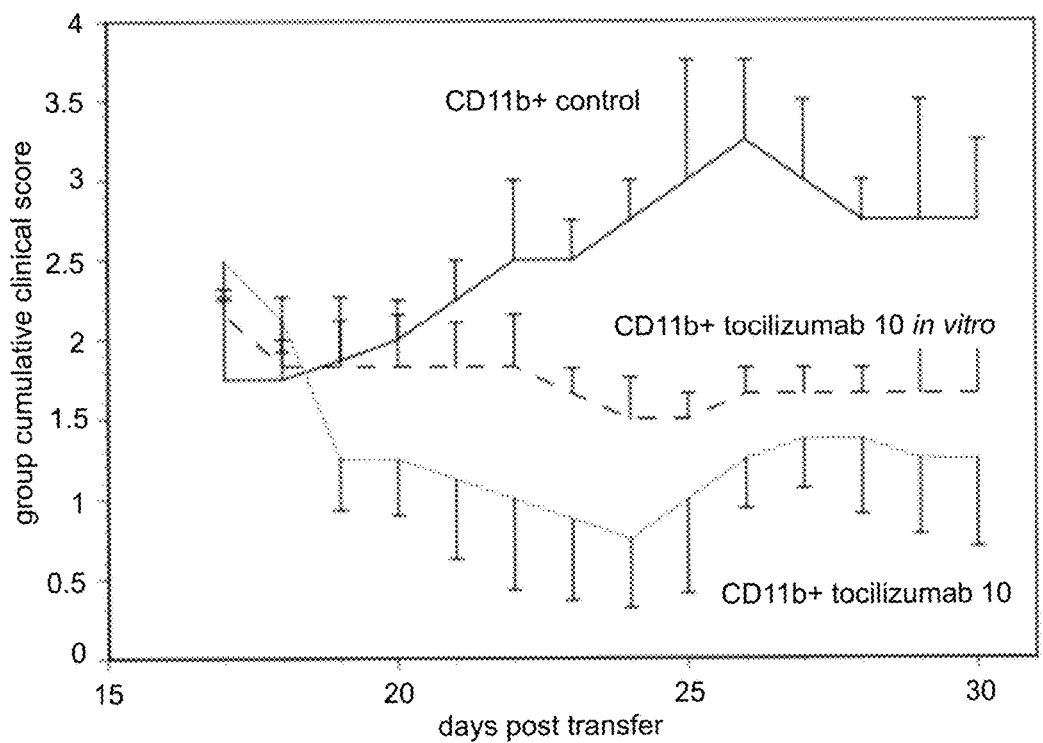
FIG. 4 shows adoptively transferred donor CD11b+ cells from tocilizumab fed immunized mice protect against active EAE. Thirty days after inoculation and after peak score of clinical attack, spleens from IgG fed control and 10 mg tocilizumab fed mice were isolated and re-stimulated with MOG peptide 35-55, CD11b+ cells isolated and adoptively transferred. A third group of control CD11b+ cells were isolated after re-stimulation with MOG peptide 35-55 and 50 mg/ml tocilizumab in vitro. Recipients of IgG control fed CD11b+ cells increased their group clinical disease severity. In contrast, recipients of tocilizumab fed CD11b+ donor cells and CD11b+ donor cells incubated with tocilizumab in vitro decreased their group clinical score significantly compared to recipients of saline control CD11b+ cells (p<0.005, days 17-30, ANOVA, group clinical score±SEM). The CD11 b+ cells from tocilizumab fed donors provided significantly better clinical protection compared to in vitro treated CD11b+ donor cells (p<0.004, t test). The in vitro control group 50 mg/ml IgG isotype control was not different from fed IgG control. This experiment shows a combination of 3 separate experiments (total n=12/group).

Whether monocyte/macrophage lineage cells ($CD11b^+$) from a fed donor would show immune-modulatory activity in actively immunized recipients was examined. After adoptive transfer of MOG-restimulated $CD11b^+$ cells isolated from MOG activated splenocytes into actively immunized recipient mice with early clinical disease on day 17 (mean group clinical score 1.7-2.5), recipients of donor $CD11b^+$ from IgG fed control mice increased their group clinical disease severity over 13 days to a maximum of 3.2. In contrast, recipients of donor $CD11b^+$ cells from 10 mg tocilizumab fed mice or from donor $CD11b^+$ cells incubated with 50 mg/ml tocilizumab in vitro decreased their group clinical score at day 30 to a score=1.7 and 1.3 respectively (FIG. 4). There was a significant improvement with 10 mg tocilizumab fed group compared to the 50 mg/ml tocilizumab in vitro group (p<0.004). Thirteen days following adoptive transfer, the number of CNS inflammatory foci in the fed $CD4^+$ T cell and $CD11b^+$ cell groups were significantly decreased compared to recipients of IgG control fed $CD4^+$ T cells and $CD11b^+$ groups (Table 1).

TABLE 1

Recipients of donor cell subsets from TCZ
fed mice have fewer inflammatory foci

|  | IgG control | 10 mg TCZ fed donor cells |
|---|---|---|
| CD4+ T cell | 37.5 ± 12.4 | 13.5 ± 3.2* |
| CD11b+ | 43.2 ± 2.8 | 10.2 ± 2.2# |

*$p < 0.008$;
$p < 0.01$;
n = 16/group.
Results are expressed as mean group inflammatory score ± SEM.

EXAMPLE 4

Figure 6:
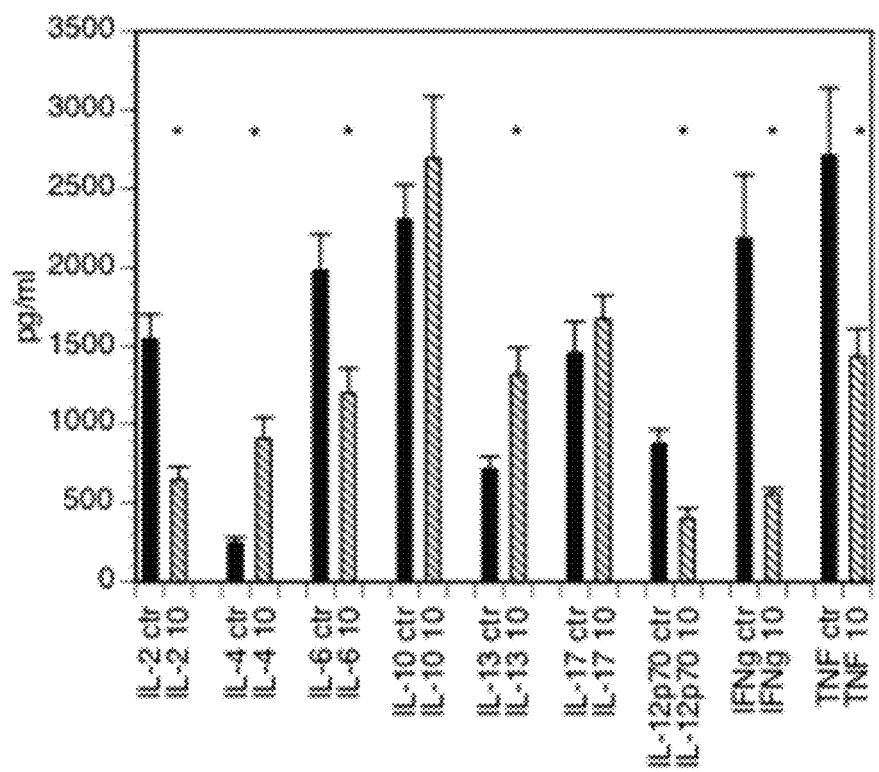
FIG. 6 shows that ingested tocilizumab decreases pro-inflammatory, Th1-like and increases Th2-like cytokines in the spleens of actively immunized mice. Lymphocytes isolated from spleen cells from IgG control fed mice or tocilizumab fed mice were stimulated with MOG peptide 35-55 and measured using an inflammatory cytokine antibody array. Splenic lymphocytes showed decreased levels of IL-6 (p<0.01, t test), TNF-α (p<0.005), Th1-like cytokines IL-2 (p<0.001), IFN-γ (p<0.001), IL-12 (p<0.005) and increased Th2-like cytokines IL-4 (p<0.001) and IL-13 (p<0.01). This experiment shows a combination of 4 separate experiments (total n=16/group). Results are expressed as pg/ml±SEM.
Figure 7:
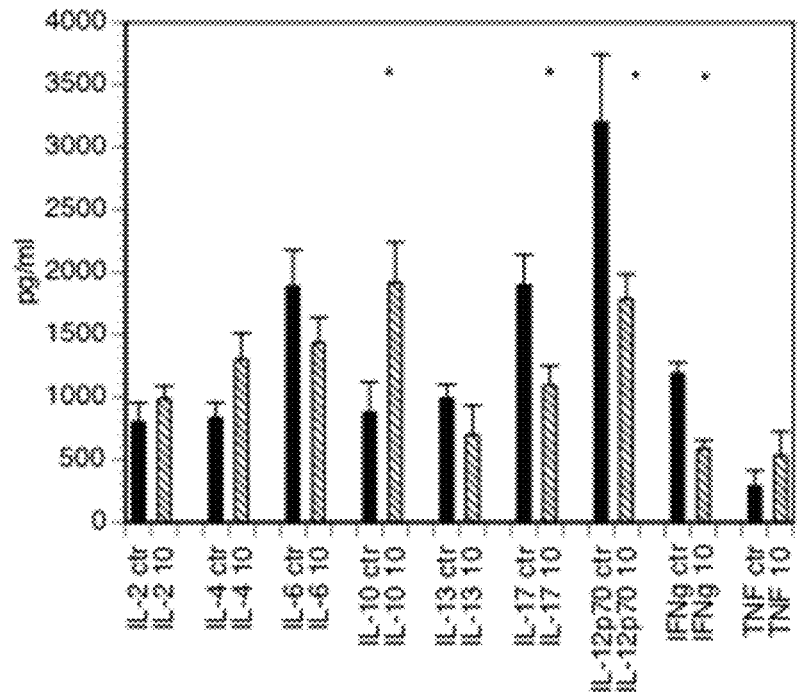
FIG. 7 shows that recipients of donor cells from tocilizumab fed mice show decreases in CNS Th1-like IFN-γ cytokines, IL-12, IL-17 and increased Th2-like IL-10. Lymphocytes isolated from spinal cords from recipients of IgG control fed or tocilizumab fed donor cells were stimulated with MOG peptide 35-55 and measured using an inflammatory cytokine antibody array as described in methods. CNS lymphocytes showed decreased levels of Th1-like cytokines IL-12 (p<0.005, t test), IL-17 (p<0.01), IFN-γ (p<0.01) and increased production of IL-10 (p<0.01) in tocilizumab dosed vs IgG control dosed mice. This experiment shows a combination of 4 separate experiments (total n=16/group). Results are expressed as pg/ml±SEM.

Oral TCZ Decreases Pro-inflammatory and Increases Counter-regulatory Cytokines in TCZ Fed Mice and Recipients of Donor Cells from TCZ Fed Mice Following clinical experiments, the effect of oral tocilizumab on cytokines in actively fed and recipients of donor cells from fed mice was examined. The cytokine profiles of MOG re-stimulated spleen and cord lymphocytes was compared in IgG fed control versus 10 mg tocilizumab fed mice. Splenic lymphocytes showed significant decreases in levels of IL-6, Th1-like cytokines IL-2, IL-12 and IFN-γ in the tocilizumab fed group compared to the IgG control fed group (FIG. 6). There was decreased TNF-α in the tocilizumab fed mice compared to the IgG control fed group. There was increased peripheral splenic lymphocyte production of IL-4 and IL-13 in tocilizumab fed vs IgG control fed mice (FIG. 6). CNS lymphocytes showed significant decreases in levels of Th1-like cytokine IFN-γ, IL-12 and IL-17 ($T_{eff}$) in the tocilizumab fed group compared to the IgG control fed group (FIG. 7).

Figure 8:
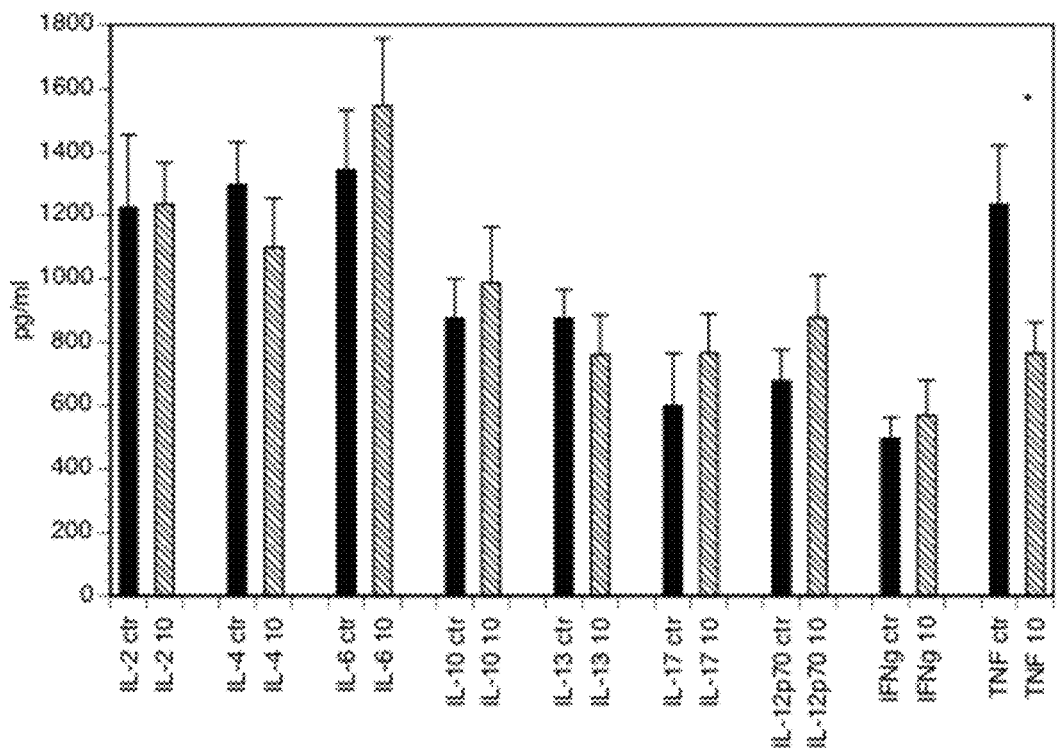
FIG. 8 shows recipients of donor cells from tocilizumab fed mice show decreases in pro-inflammatory TNF-α. Lymphocytes isolated from spleens from recipients of IgG control fed or tocilizumab fed donor cells were stimulated with MOG peptide 35-55 and measured using an inflammatory cytokine antibody array. Splenic lymphocytes showed decreased levels of TNF-α (p<0.01, t test) in tocilizumab dosed vs mock dosed mice. This experiment shows a combination of 4 separate experiments (total n=16/group). Results are expressed as pg/ml±SEM.
Figure 9:
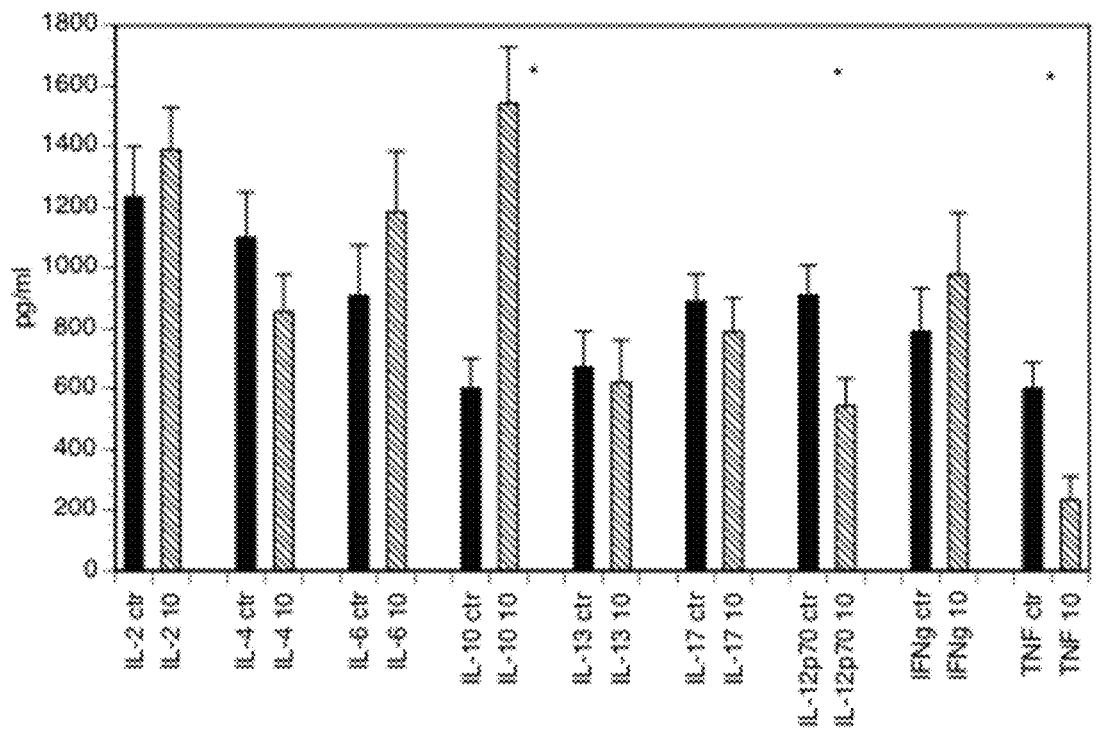
FIG. 9 show that recipients of donor cells from tocilizumab fed mice show decreases in CNS pro-inflammatory, Th1-like cytokines, and increased Th2-like IL-10. Lymphocytes isolated from spinal cords from recipients of IgG control fed or tocilizumab fed donor cells were stimulated with MOG peptide 35-55 and measured using an inflammatory cytokine antibody array. CNS lymphocytes showed decreased levels of TNF-α (p<0.01, t test), Th1-like cytokines IL-12 (p<0.01) and increased production of MOG induced IL-10 (p<0.001) in tocilizumab dosed vs IgG control dosed mice. This experiment shows a combination of 4 separate experiments (total n=16/group). Results are expressed as pg/ml±SEM.

The cytokine profiles of MOG re-stimulated spleen and cord lymphocytes in recipients of IgG control fed vs tocilizumab fed donor cells was examined. Splenic lymphocytes showed a significant decrease in levels of TNF-60 in tocilizumab fed groups compared to the IgG control fed group (FIG. 8). CNS lymphocytes showed significant decreases in IL-12 and TNF-α and increases in IL-10 in the tocilizumab fed group compared to the IgG control fed group (FIG. 9).

EXAMPLE 5

Recipients of TCZ Fed Spleen CD4+ T Cells Produce Less IL-12 and Recipients of TCZ Fed Spleen CD11b+ Cells Produce Less IL-12 but more IL-10 and IL-13

Figure 10:
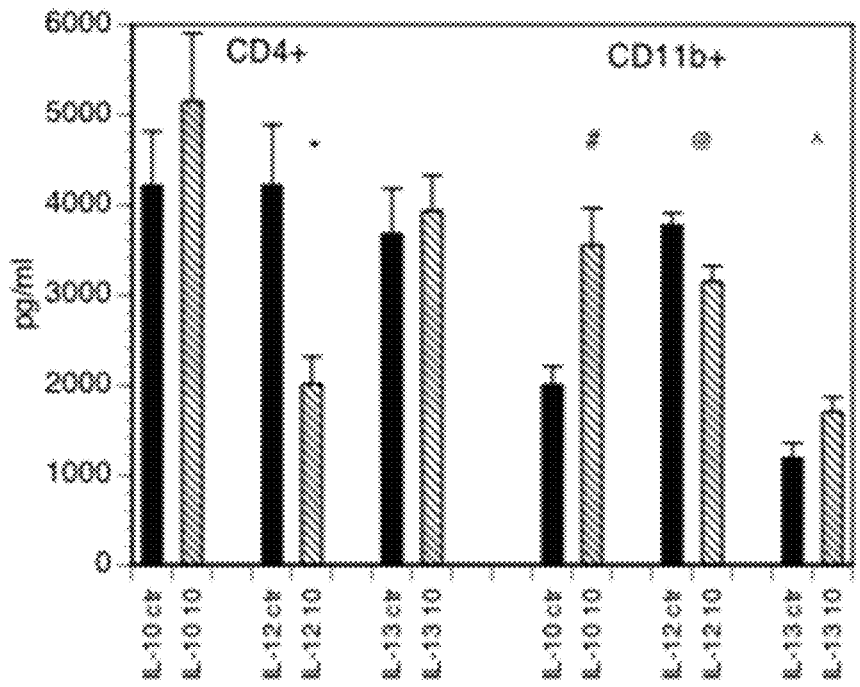
FIG. 10 shows recipients of tocilizumab fed spleen CD4+ T cells produce less IL-12 and tocilizumab fed spleen CD11b+ cells produce less IL-12 but more IL-10 and IL-13 compared to IgG control fed donor cells. The cytokine profiles of MOG re-stimulated spleen lymphocytes were investigated in recipients of IgG fed CD4+ T cells or CD11b+ vs tocilizumab fed CD4+ T cells or CD11b+ donor cells (from FIGS. 3 and 4). Recipient splenic lymphocytes showed significant decrease in levels of IL-12 after both CD4+ T cells (left) and CD11b+ cells (right) transfer compared to the IgG fed group. Splenic lymphocytes showed significant increases in IL-10 and IL-13 in the CD11b+ cell tocilizumab fed group compared to the CD11b+ cells IgG fed group. There were no significant changes in IL-2, IL-4, IL-6, IL-17, IFN-γ or TNF-α in recipient spleen after CD4+ T cell or CD11b+ cells from TCZ fed donors (data not shown). Results are expressed as pg/ml±SEM. * p<0.001, @ p<0.03, # p<0.01, ^ p<0.05; all t test.

Whether lymphocyte subsets showed differential activity on cytokine profiles was determined by investigating the cytokine profiles of MOG re-stimulated spleen lymphocytes in recipients of IgG control fed CD4+ T cells or CD11b+ vs TCZ fed CD4+ T cells or CD11b+ donor cells (from FIGS. 3 and 4). Recipient splenic lymphocytes showed significant decreases in levels of IL-12 after both CD4+ T cells and CD11 b+ transfer in tocilizumab fed groups compared to the IgG fed group. Splenic lymphocytes also showed significant increases in IL-10 and IL-13 in the CD11b+ tocilizumab fed group compared to the CD11b+ IgG fed group (FIG. 10). There were no significant changes in IL-2, IL-4, IL-6, IL-17, IFN-γ or TNF-α in recipient spleen after CD4+ T cell or CD11 b+ from tocilizumab fed donors.

EXAMPLE 6

Spleen cell of recipients of TCZ in vitro treated splenic lymphocytes show decreased IFN-γ and IL-12

Whether in vitro treatment had similar effects on cytokines compared to in vivo feeding was determined. After TCZ in vitro treatment of whole splenocytes from control IgG fed donors, recipient spleen cells had decreased IFN-γ secretion and IL-12 compared to IgG isotype control treated cells (Table 2). Recipient spinal lymphocytes had decreased IFN-γ secretion compared to IgG isotype control treated cells (Table 2). There were no significant changes in IL-2, IL-4, IL-6, IL-10, IL-13, IL-17 or TNF-α.

TABLE 2

Spleen cells in recipients of TCZ in vitro treated
splenic lymphocytes show decreased IFN-γ and IL-12.

|  |  | IgG control | Recipients of 50 mg/ml TCZ in vitro treated donor cells |
|---|---|---|---|
| IFN-γ | Spleen | 520 ± 96 | 40 ± 12* |
|  | CNS | 540 ± 96 | 54 ± 14* |
| IL-12 | Spleen | 720 ± 128 | 292 ± 48* |
|  | CNS | 530 ± 143 | 450 ± 88 |

*$p < 0.001$;
n = 16/group.
Results are expressed as pg/ml ± SEM.

EXAMPLE 7

Actively Tcz fed or recipients of Tcz fed cells show no significant increase in CD4+CD25+FoxP3+ cell frequency or TGF-β secretion.

Whether immunomodulation was due to increase $T_{reg}$ frequency or increased TGF-bβ secretion was determined by examining whether CD4+CD25+ FoxP3+ $T_{reg}$ might be induced by TCZ feeding and explain protection in actively treated and recipients of adoptively transferred cells from TCZ fed donors. FACS analysis shows no significant increase in CD4+CD25+FoxP3+ cell frequency in TCZ fed compared to IgG control fed mice in actively fed or recipients of actively fed donor cells.

Whether there was increased secretion of TGF-β was examined in MOG re-stimulated spleen and cord lymphocytes from actively treated and recipients of adoptively transferred cells from tocilizumab fed donors. There was no effect on TGF-β secretion after active tocilizumab feeding in spleen or in spinal lymphocytes compared to control (Table 3). There was also no effect on TGF-β secretion in spleen or in spinal lymphocytes from recipients of tocilizumab feed donors compared to control.

TABLE 3

No effect on TGF-β secretion after active TCZ
feeding or from recipients of TCZ feed donors

|  | IgG control | TCZ fed or recipient |
|---|---|---|
| Spleen active | 537 ± 171 | 635 ± 257 |
| CNS active | 215 ± 84 | 217 ± 67 |
| Spleen adoptive transfer | 350 ± 72 | 557 ± 150 |
| CNS adoptive transfer | 269 ± 29 | 303 ± 88 | n = 16/group.
Results are expressed as pg/ml ± SEM.

Discussion

The present invention demonstrates an overall anti-inflammatory effect of ingested tocilizumab in MOG immunized mice. Both 1 mg and 10 mg ingested (oral) tocilizumab showed a significant clinical effect with 10 mg demonstrating the most robust activity. Adoptive transfer of tocilizumab fed or in vitro tocilizumab treated MOG-restimulated splenocytes, CD4+ T cells or CD11b+ into recipient mice with early clinical disease suppressed ongoing disease. Both active treatment with oral tocilizumab or adoptive transfer of splenocytes, CD4+ T cells and CD11b+ from tocilizumab fed or in vitro treated mice showed significantly less CNS inflammation in the tocilizumab groups. There was a significant improvement in clinical scores with 10 mg tocilizumab fed CD11b+ donor cells in recipients compared to the 50 mg/ml tocilizumab in vitro group suggesting a unique effect from feeding.

Overall, there was a decrease in innate inflammatory cytokines TNF-α, Th1-like cytokine IL-12p70 in spleen and CNS as well as increases in one or more Th2-like counter-regulatory cytokines, including IL-4, IL-10, or IL-13 in active fed spinal cords and adoptive transfer recipient spinal cords. More specifically, there was a significant decrease in IL-6 secretion in tocilizumab fed spleen cells. The most potent and specific cytokine activity was found with CD11b+ cells that showed decreased IL-12 activity and increased IL-10 and IL-13 activity.

Investigators have differed on the effect of IL-6 in EAE. IL-6 transgenic mice develop neurologic disease (20) and IL-6-deficient mice are resistant to EAE (21). However, parenteral IL-6 can accelerate recovery from EAE attacks, reduces subsequent EAE, TNF-α and class II CD4+ cells while increasing IL-10 (24).

In contrast to the variable direct effects of IL-6, parenteral anti-IL-6R mAb reduces the development of actively induced and adoptive EAE inflammatory infiltrates despite increased levels of CSF IL-6 (25). Parenteral anti-IL-6R mAb (clone MR16-1) inhibits EAE and MOG peptide-specific CD4+, CD8+, and Th17 T cells but not when given after disease onset in contrast to the present invention (26). Decreased IL-6 levels in actively fed spleen cells showed an anti-IL-6 effect. Oral administration may provide access to the gut associated immune-regulatory populations and perhaps the spleen critical in controlling ongoing disease.

Adoptive transfer of EAE with TNF-α producing cells contributes to CNS inflammation (27, 28). TNF-α is important in CNS pathology in EAE (29), induces EAE (30, 31) as part of a functional 'type 1 cytokine' unit (32). The reduction of TNF activity reduces severity of EAE (33).

However, it is unclear whether blockade of IL-6 directly reduces TNF in immune compartments. A modest literature suggests that IL-6 inhibits TNF production (34) in general and in EAE (24). An abrogation of IL-6 activity would have the opposite effect. In this model, oral IL-6 receptor antibody inhibits TNF production.

Macrophage-derived IL-12 activates encephalitogenic T cells in vivo and increases the ratio of CD11b+ to T cells in brain (35). IL-12 stimulates myelin-reactive T cells to up-regulate CCR5 and correlates with CNS-infiltrating and encephalitogenic properties (36). IL-12 drives antigen specific cells (37) important in CNS inflammation (38) and contributes to macrophage mediated disease exacerbation (35). Antibody inhibition of endogenous IL-12 in vivo after transfer prevents paralysis (39).

A reciprocal modulation of the IL-10 and IL-12 cytokine circuit in vivo helps inhibit the progression of disease in active CNS (40). The disease-promoting effects of IL-12 may be antagonized by IL-10 produced (41) by TCZ fed donor CD11b+ cells. Decreased IL-12 production in active and recipient's CNS of TCZ fed donor cells supports this notion. CD11c+CD11b+ DCs with increased Th2 IL-10 and decrease IL-12 inhibit MOG-specific T cells by increasing CD4+CD25+Foxp3+ regulatory T cells and TGF-β (42).

CD11b+ cells from TCZ fed spleens inhibited active disease by directly increasing IL-10 in recipient CNS without increased $T_{reg}$ or TGF-β. Others have shown that two sets of Peyer's patch (PP) DC cells can express high levels of CD11b+; CD8a-CD4- or CD8a+CD4- and induce IL-10 producing naive T cells (43).

Th2-like lymphocytes produce IL-4 (44), IL-10 and IL-13 (44) 5 and inhibit EAE (45) Splenic IL-13 reduces infiltrating mononuclear cells into CNS during EAE (46) and IL-13 can inhibit PBMC production of IL-12 (47). CD11b+ cells from TCZ fed donors have already undergone IL-13 exposure from splenocytes (FIG. 6) and spleen CD11 b+ cells (FIG. 10) in active treated spleens. These IL-13 producing cells once transferred modulate active disease in recipients showing that IL-13 may down-regulate monocyte/macrophage activities at sites of inflammation (48). The combination of CD4+ T cells and CD11b+ (i.e., ~splenic lymphocytes) decrease both TNF-α/IL-12 and increase IL-10 production in recipient CNS. CD4+ T cells can produce more IL-13 in donor spleens thereby degrading subsequent antigen presentation in recipients.

The clinical effect of in vitro TCZ splenocytes and CD4+ T cells is less robust than feeding and limited to exclusive inhibition of Th1-like cytokines IFN-γ and TNF-α. There is a broader anti-inflammatory effect (decreased IL-12/increased IL-10 and IL-13) of in vivo tocilizumab shown in particular after CD11b+ transfer. The present invention shows that an oral monoclonal antibody against IL-6 has intrinsic immune activity superior to in vitro activity without systemic induction of Treg cells or Th3 cells (49).

The predominant effect of IL-6 is to induce immunity. When IL-6 is depleted in tocilizumab RA responders in the periphery, circulating myeloid DC are reduced without changes in plasmacytoid DC, CD4+ T cells, and CD8+ T cells (50, 51). IL-6 in conjunction with other factors can generate dendritic cells (DC) (52, 53) and expand human bone marrow derived CD34+ precursors into effective APCs (54). IL-6 is critical for murine Ag-specific T cell activating CD11c+ DC functions (55) and mobilization of CD8+ and CD11b+ DC to murine LN (56). Decreased IL-6 production in tocilizumab fed spleen cells suggesting interaction with GALT or spleen. Others have found that decreased IL-6 results in increased IL-13 in EAE (46).

Oral tocilizumab may be absorbed and block IL-6 in CD11b+ in spleen. tocilizumab could also interact with the immune-modulatory GALT cells. Examination of GALT cell populations after anti-IL-6 administration will be important in defining the mechanism of action (MOA) of this molecule by the oral route. Because oral tocilizumab shows activity in an animal model of multiple sclerosis, it would be a good candidate for the treatment of multiple sclerosis despite concerns about anti-IL-6 and demyelinating disease.

The following references are cited herein:
1. Alvord et al., Ann NY Acad Sci. 1965; 122:333-45.
2. Raine et al., NY State J Med. 1977; 77:1693-6.
3. Wisnewski et al., Ann Neurol. 1977; 1:144-8.
4. Feuer et al., J Neuroimmunol. 1985; 10:159-66.
5. Brod et al., Neurology. 1994 June; 44:1144-8.
6. Brod et al., J Neuroimmunol. 2007 February; 183:89-95.
7. Brod et al., J Neuroimmunol. 2008 January; 193:106-12.
8. Brod et al., J Neuroimmunol. 2011 March; 232:131-5.
9. Brod et al., Autoimmunity. 2011 August; 44:437-43.
10. Brod et al., J Interferon Cytokine Res. 1995 February; 15:115-22.
11. Paul-Pletzer K. Drugs Today (Barc). 2006 September; 42:559-76.

12. Nishimoto et al., Handbook of experimental pharmacology. 2008:151-60.
13. Yokota et al., Clinical reviews in allergy & immun. 2005 June; 28:231-8.
14. Smolen et al., Lancet. 2008 Mar. 22; 371:987-97.
15. Nishimoto et al., Ann Rheum Dis. 2007 September; 66:1162-7.
16. Scheinecker et al., Drug discovery. 2009 April; 8:273-4.
17. Araki et al., Modern rheumatology 2013 July; 23:827-31.
18. Kaly et al., Clinical rheumatology. 2012 February; 26:157-65.
19. Uchiyama et al., Biological & pharma. bulletin. 2008 June; 31:1159-63.
20. Campbell et al., Proc Nat Acad Sci USA. 1993; 90:10061-5.
21. Samoilova et al., Journal of immunology. 1998 Dec. 15; 161:6480-6.
22. Willenborg et al., Scand J Immunol. 1995 January; 41:31-41.
23. Tompkins et al., Journal of immunology. 2002 Apr. 15; 168:4173-83.
24. Di Marco et al., J Neuroimmunol. 2001 Jun. 1; 116:168-77.
25. Gijbels et al., Mol Med. 1995 November; 1: 795-805.
26. Serada et al., Proc Natl Acad Sci USA. 2008 Jul. 1; 105:9041-6.
27. Waldburger et al., Am J Pathol. 1996; 148:375-82.
28. Held et al., J Autoimmun. 1993 June; 6:311-22.
29. Renno et al., Journal of immunology. 1995; 154:944-53.
30. Issazadeh et al., J Neurosci Res. 1995; 40:579-90.
31. Okuda et al., J Interferon Cytokine Res. 1998 June; 18:415-21.
32. Qiu et al., Am J Pathol. 2001 April; 158:1503-15.
33. Selmaj et al., Ann Neurol. 1991; 30:694-700.
34. Aderka et al., 1989 Dec. 1; 143:3517-23.
35. Smith et al., Am J Path. 1997; 150:1909-17.
36. Bagaeva et al., J Neuroimmunol. 2003 April; 137:109-16.
37. Segal et al., Journal of experimental medicine. 1996; 184:771-5.
38. Issazadeh et al., J Neuroimmunol. 1996; 69:103-15.
39. Leonard et al., Journal of experimental medicine. 1995; 181:381-6.
40. Tuohy et al., J Neuroimmunol. 2000 Nov. 1; 111:55-63.
41. Segal B et al., Journal of experimental med., 1998 Feb. 16; 187:537-46.
42. Li et al., Journal of immunology. 2008 Aug. 15; 181: 2483-93.
43. Kelsall et al., Immunol Rev. 2005 August; 206:132-48.
44. Malefyt et al., Journal of experimental medicine. 1991; 174:915-24.
45. Monney et al., Nature. 2002 Jan. 31; 415:536-41.
46. Offner et al., Journal of immunology. 2005 Sep. 15; 175:4103-11.
47. D'Andrea et al., Journal of Experimental Med., 1995 Feb. 1; 181:537-46.
48. Hart et al., Clin Exp Immunol. 1995 March; 99:331-7.
49. Inobe et al., Eur J Immunol. 1998; 28:2780-90.
50. Richez et al., J Rheumatol. 2012 June; 39:1192-7.
51. Marti et al., Ann N Y Acad Sci. 2009 September; 1173:334-42.
52. Encabo et al., Stem Cells. 2004; 22:725-40.
53. Fadilah et al., Stem cells and development. 2007 October; 16:849-55.
54. Bernhard et al., Experimental hematology. 2000 April; 28:365-72.
55. Bleier et al., Journal of immunology. 2004 Jun. 15; 172:7408-16.
56. Dawicki et al., Journal of immunology. 2010 Feb. 15; 184:2116-23.

While the invention has been described with reference to certain embodiments, those skilled in the art will appreciate that modifications may be made without departing from the scope of the invention. All patents and publications cited in this specification are indicative of the level of those skilled in the art to which the invention pertains.

What is claimed is:

1. A method for treating or delaying the onset of an autoimmune condition in a human subject comprising orally administering tocilizumab to the subject; wherein said autoimmune condition is multiple sclerosis or rheumatoid arthritis.

2. The method of claim 1, wherein the tocilizumab is administered in a liquid form.

3. The method of claim 1, wherein the tocilizumab is administered in a solid form.

4. The method of claim 1, wherein tocilizumab is administered in a dose from 1.0 μg to 50 μg.

5. The method of claim 4, wherein tocilizumab is administered in a dose from 1 μg to 10 μg.

6. The method of claim 1, wherein said tocilizumab administration decreases levels of IL-6, Th1-like cytokines IL-2, IL-12, TNF-α and IFN-γ.

7. The method of claim 1, wherein said tocilizumab administration increases levels of IL-4, IL-10 and IL-13.

8. The method of claim 1, further comprising administering a compound selected from the group consisting of a SIRS peptide, α-MSH, ACTH and SST.

9. A method for decreasing innate inflammatory cytokines IL-1β and TNF-α, Th1-like cytokines IL-2 and IFN-γ, IL-17 ($T_{eff}$), IL-12p70 and increasing the Th2-like counter-regulatory cytokine IL-13 in a human subject comprising orally administering tocilizumab to the subject.

10. The method of claim 9, wherein the tocilizumab is administered in a liquid form.

11. The method of claim 9, wherein tocilizumab is administered in a solid form.

12. The method of claim 9, wherein tocilizumab is administered in a dose from 1.0 μg to 50 μg.

13. The method of claim 12, wherein tocilizumab is administered in a dose from 1 μg to 10 μg.

14. The method of claim 9, further comprising administering a compound selected from the group consisting of a SIRS peptide, α-MSH, ACTH and SST.

* * * * *